(12) United States Patent
Molin et al.

(10) Patent No.: US 8,586,026 B2
(45) Date of Patent: Nov. 19, 2013

(54) BACTERIAL DIVERSITY

(75) Inventors: Goran Molin, Lund (SE); Siv Ahrne, Lund (SE); Caroline Karlsson, Lund (SE); Bengt Jeppsson, Lund (SE)

(73) Assignee: Probi AB, Lund (SE)

( * ) Notice: Subject to any disclaimer, the term of this patent is extended or adjusted under 35 U.S.C. 154(b) by 571 days.

(21) Appl. No.: 12/529,498

(22) PCT Filed: Feb. 29, 2008

(86) PCT No.: PCT/SE2008/000170
§ 371 (c)(1),
(2), (4) Date: Feb. 4, 2010

(87) PCT Pub. No.: WO2008/105715
PCT Pub. Date: Sep. 4, 2008

(65) Prior Publication Data
US 2010/0143463 A1     Jun. 10, 2010

(30) Foreign Application Priority Data

Mar. 1, 2007 (SE) ..................... 0700551

(51) Int. Cl.
*A01N 63/00*     (2006.01)
(52) U.S. Cl.
USPC ........ 424/93.45; 424/463; 424/474; 424/490; 435/252.9; 435/857
(58) Field of Classification Search
None
See application file for complete search history.

(56) References Cited

FOREIGN PATENT DOCUMENTS

| JP | 09-002959 A | 1/1997 |
|---|---|---|
| JP | 2006-296307 A | 11/2006 |
| WO | WO 2006/038869 A1 | 4/2006 |
| WO | WO 2006041930 A2 | 4/2006 |
| WO | WO 2007/003917 A1 | 1/2007 |
| WO | WO 2007004966 A1 | 1/2007 |

OTHER PUBLICATIONS

Ott et al., Gut, 2004, vol. 53, p. 685-693.*
Schultz et al., Inflammatory Bowel Diseases, 2002, vol. 8, No. 2 p. 71-80.*
Sepehri et al., Inflamm. Bowel Dis., Feb. 2007, vol. 13, p. 675-683.*
Wang et al., Journal of Microbiological Methods, 2004, vol. 59, p. 53-69.*
Schultz et al., Inflammatory Bowel Diseases, 2002, vol. 8, No. 2, p. 71-80.*
European Patent Office, Office Action in related European Patent Application No. 08 741 827.3, dated Dec. 6, 2012.
De Las Rivas, B. et al. 2006 "Development of a Multilocus Sequence Typing Method for Analysis of *Lactobacillus plantarum* Strains" *Microbiology* 152:85-93.
Hayashi, H. et al. 2005 "Molecular Analysis of Jejunal, Ileal, Caecal and rectosigmoidal Human Colonic Microbiota Using 16S rRNA Gene Libraries and Terminal Restriction Fragment Length Polymorphism" *J Med Microbiol* 54:1093-1101.
Krause, D.O. et al. 1995 "Effect of Weaning Diet o the Ecology of Adherent Lactobacilli in the Gastrointestinal Tract of the Pig." *Journal Anim Sci* 73:2347-2354.
Niedzielin, K. et al. 2001 "A Controlled, Double-Blind, Randomized Study on the Efficacy of *Lactobacillus plantarum* 299V in Patients with Irritable Bowel Syndrome" *European Journal of Gastroenterology & Hepatology* 13(10)1143:1147.
Camilleri, M. 2001 "Management of the irritable bowel syndrome" *Gastroenterology* 120: 652-668.
Karlsson, C. et al. 2009 "Probiotic therapy to men with incipient arteriosclerosis initiates increased bacterial diversity in colon: A randomized controlled trial" *Atherosclerosis* 208(1): 228-233.
Nobaek, S. et al. 2000 "Alteration of intestinal microflora is associated with reduction in abdominal bloating and pain in patients with irritable bowel syndrome" *The American Journal of Gastroenterology* 95: 1231-1238.
Goossens D.A.M. et al. 2006 "The effect of a probiotic drink with *Lactobacillus plantarum* 299v on the bacterial composition of faeces and mucosal biopsies of rectum and ascending colon" *Aliment Pharmacol Ther* 23:255-263.
Office Action in corresponding Japanese Application No. 2009-551968, dated Feb. 28, 2013.
Osman, N. et al. 2004 "Modulation of the effect of dextran sulfate sodium-induced acute colitis by the administration of different probiotic strains of *Lactobacillus* and *Bifidobacterium*" *Digestive Diseases and Sciences* 49:320-327.
Pathmakanthan S. et al. 2004 "*Lactobacillus plantarum* 299: Beneficial in vitro immunomodulation in cells extracted from inflamed human colon" *J Gastroenterology and Hepatology* 19:166-173.

\* cited by examiner

*Primary Examiner* — Kade Ariani
(74) *Attorney, Agent, or Firm* — Knobbe, Martens, Olson & Bear, LLP

(57) ABSTRACT

Use of one strain of *Lactobacillus plantarum* for the manufacture of a composition for increasing the diversity of the gastrointestinal tract by administration of said strain to an individual with a view to producing an increased diversity index compared to placebo is disclosed, as well as use of one strain of *Lactobacillus plantarum* for the manufacture of a composition for prophylactic treatment of a healthy individual against developing a low bacterial diversity (LBD); of an individual having LBD against developing one or more physiologically disturbed conditions, large intestine bacterial overgrowth (LIBO) or small intestine bacterial overgrowth (SIBO); and of an individual having LIBO or SIBO against developing one or more physiologically disturbed conditions, and a method for increasing said diversity.

14 Claims, 1 Drawing Sheet

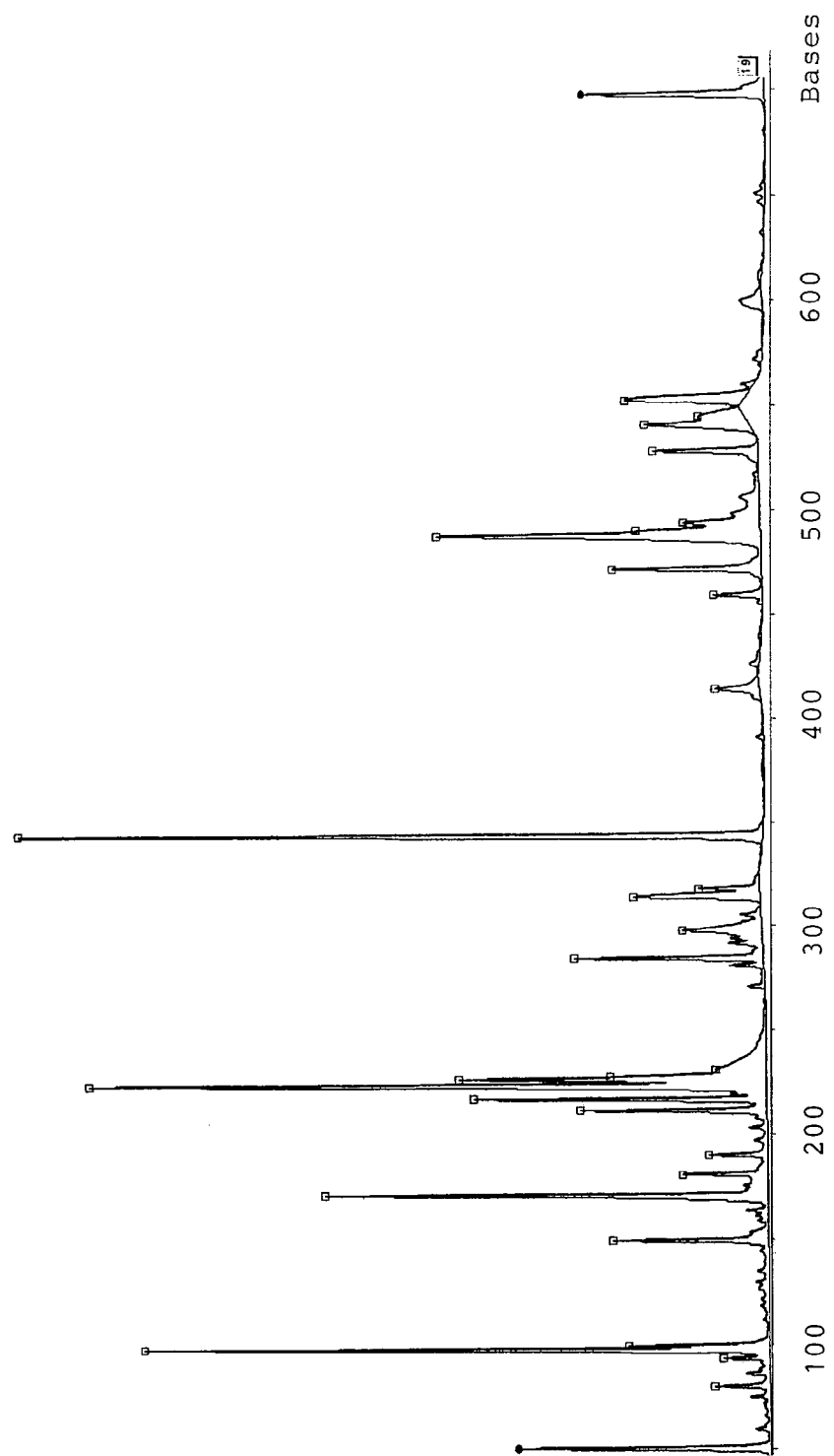

BACTERIAL DIVERSITY

RELATED APPLICATIONS

This application is a U.S. National Phase of International Application No. PCT/SE2008/000170/000190, filed Feb. 29, 2008, designating the U.S. and published in English on Sep. 4, 2008 as WO 2008/105715, which claims the benefit of Swedish Application No. SE 0700551-5, filed Mar. 1, 2007.

TECHNICAL FIELD OF THE INVENTION

The present invention relates to the use of one strain of *Lactobacillus plantarum* for the manufacture of a composition for increasing the diversity of the gastrointestinal tract and to the use of one strain of *Lactobacillus plantarum* for the manufacture of a composition for prophylactic treatment.

BACKGROUND ART

It is a general consensus in biology that a high diversity (variation of different types of organisms) is beneficial for the global ecosystem as well as for local more limited ones, and also for the individual human being. A high diversity indicates that the ecosystem is in healthy balance. In contrast, an unbalanced or disturbed, or diseased, ecosystem opens up for "overgrowth" of a few organisms, taking over the system and causing further disturbances and new diseased conditions. This also applies to the ecosystem of the human gut.

The bacterial flora of the human gastrointestinal (GI) tract is a complex ecosystem. The composition and activity of the bacterial flora play important roles in human health due to its contribution to nutrition, development and constant tuning of the immune system, and colonization resistance. The GI tract can be regarded as a specialized tube extending from the mouth to the anus. It is divided into several well-defined anatomical regions, including mouth, oesophagus, stomach, small intestine (duodenum, jejunum and ileum), and large intestine (caecum, colon and rectum). The bacterial concentrations in the stomach and upper two thirds of the small intestine (duodenum and jejunum) are relatively low because of the acidity in the stomach, short transit time of content, secretion of bile and pancreatic juice. The concentration is normally in the range of $10^2$ to $10^4$ colony forming units of bacteria (cfu) per ml of gastric or intestinal content, and examples of typical resident bacteria in these regions are *Streptococcus* and *Lactobacillus*. The distal part of the small intestine (ileum) has normally a concentration of $10^7$-$10^8$ cfu per ml and is usually dominated by the same types of bacteria that are found in colon, i.e. different classes of Firmicutes, Bacteriodetes, Fusobacteria, Verrucomicrobia, Proteobacteria and *Bifidobacterium* (WANG, M., AHRNÉ, S., JEPPSSON, B. & MOLIN, G. (2005). Comparison of bacterial diversity along the human intestinal tract by direct cloning and sequencing of 16S rRNA genes. *FEMS Microbial Ecology* 54: 219-231). The highest bacterial concentration is found in the large intestine because of the longer transit time (up to 60 h). It has been estimated that bacterial biomass makes up 40-55% of the faecal solids, and the concentration of live bacteria is normally around $10^{10}$-$10^{11}$ cfu per g of intestinal content. In an undisturbed, balanced and healthy colon also the bacterial diversity is at its peak. However, due to the extremely high bacterial concentration, the colon is also the part of the GI tract that is most vulnerable for translocation where live bacteria or toxic parts of bacteria pass through the mucosal barrier and into the mesenteric lymph nodes and other extra-intestinal sites, such as the spleen, liver, kidney, peritoneal cavity and bloodstream. Low bacterial diversity (LBD) increases the risk of large intestinal bacterial overgrowth (LIBO) and small intestinal overgrowth (SIBO), which may lead to translocation.

It has been demonstrated in the technical field that the diversity of the gastrointestinal tract in patients with Crohn's disease is low, [Manichanh C., Rigottier-Gois L., Bonnaud E., Gloux K., Pelletier E., Frangeul L., Nalin R., Jarrin C., Chardon P., Marteau P., Roca J., and Doré J. (2006) Reduced diversity of faecal microbiota in Crohn's disease revealed by a metagenomic approach. Gut 55:205-211] [Ott S. J. Musfeldt M., Wenderoth D. F., Hampe J., Brant O., Fölsch U. R., Timmis K. N., and Schreiber S. (2004) Reduction in diversity of the colonic mucosa associated bacterial microflora in patients with active inflammatory disease. Gut 53:685-693].

It has further been demonstrated that newborn with a low diversity in the gastrointestinal tract run a greater risk to become allergic, [Wang, M., Karlsson, C., Olsson, C., Adlerberth, I., Wold, A., Strachan, D. P., Martricardi, P. M., Åberg, N., Perkin, M. R., Tripodi, S., Hesselmar, B., Saalman, R., Molin, G. & Ahrné, S. (2008). Reduced diversity in the early fecal microbiota of infants developing atopic eczema: Low diversity in early microbiota of infants developing atopy. Journal of Allergy and Clinical Immunology 121:129-134.

It has further been demonstrated that female rats suffering from "overgrowth" (low diversity) in the gastrointestinal tract gave birth to babies with an enhanced haptoglobin level and immature intestine, [FÅK, F., Ahrné, S., Molin, G., Jeppsson, B. & Weström, B (2008). Microbial manipulation of the rat dam changes bacterial colonization and alters properties of the gut in her offspring. American Journal of Physiology—Gastrointestinal and Liver Physiology 294: 148-154.

Thus, there seems to be a connection between low diversity in the gastrointestinal tract and several physiologically disturbed conditions in human beings and other mammals.

It is known that the use of antibiotics lowers the bacterial diversity in the gastrointestinal tract. Since the use of antibiotics is huge worldwide there is indeed a need within the technical field to provide novel ways to overcome this problem of low diversity in the gastrointestinal tract, said low diversity affecting the general health of mankind.

It is further generally known that the lifestyle of mankind in developed countries causes many unhealthy disturbances and conditions such as cardiovascular diseases in view of e.g. stress and overweight. It is known that people with these disturbances and conditions often have a low bacterial diversity in the gastrointestinal tract.

Thus, there is a need within the technical field to overcome the problem of physiologically disturbed conditions related to or due to low diversity in the gastrointestinal tract of individuals.

WO 01/11077 A2 discloses methods of diagnosing or treating irritable bowel syndrome and other disorders caused by small intestinal bacterial overgrowth (SIBO) by administration of anti-microbial or probiotic agents, e.g. a species of *Bifidobacterium* or *Lactobacillus*, or normalizing intestinal motility by employing a prokinetic agent.

SUMMARY OF THE INVENTION

The above mentioned problems are solved by the present invention.

The present invention relates, in one aspect, to the use of one strain of *Lactobacillus plantarum* for the manufacture of a composition for increasing the bacterial diversity of the gastrointestinal tract by administration of said strain to an individual with a view to producing an increased diversity index difference compared to placebo.

The present invention relates, in a further aspect, to the use of one strain of *Lactobacillus plantarum* for the manufacture of a composition for prophylactic treatment of a healthy individual against developing a low bacterial diversity (LBD); of an individual having LBD against developing physiologically disturbed conditions, large intestine bacterial overgrowth (LIBO) or small intestine bacterial overgrowth (SIBO); and of an individual having LIBO or SIBO against developing physiologically disturbed conditions.

The invention further relates to a method for increasing the bacterial diversity of the gastrointestinal tract by administration of one strain of *Lactobacillus plantarum* to an individual to produce an increased diversity index difference compared to placebo.

The present invention also relates to the treatment of one or a wide array of physiologically disturbed conditions based on a low bacterial diversity (LBD) in the gastrointestinal (GI) tract of an individual, optionally induced via small intestinal bacterial overgrowth (SIBO) and/or large intestine bacterial overgrowth (LIBO), by improving and/or increasing the bacterial diversity and eradicating small intestinal bacterial overgrowth (SIBO) and large intestinal bacterial overgrowth (LIBO) in the gut.

Further, the present invention also relates to a *Lactobacillus plantarum* strain for use in the production of an increased diversity index difference as defined in any one of claims 1-13 and/or for use in prophylactic treatment as defined in any one of claims 14-25.

BRIEF DESCRIPTION OF THE DRAWINGS

FIG. 1 depicts the T-RFLP profile of HaeIII-digested 16S rRNA genes amplified from human mucosa.

DEPOSIT OF MICROORGANISM

The following microorganisms have been deposited in accordance with the terms of the Budapest Treaty with the Deutsche Sammlung von Mikroorganismen and Zellkulturen GmbH (DSMZ), Braunschweig, Germany, on the dates indicated:

| Microorganism | Accession No. | Date |
| --- | --- | --- |
| *Lactobacillus plantarum* 299 | DSM 6595 | Jul. 2, 1991 |
| *Lactobacillus plantarum* 299v | DSM 9843 | Mar. 16, 1995 |
| *Lactobacillus plantarum* HEAL9 | DSM 15312 | Nov. 27, 2002 |
| *Lactobacillus plantarum* HEAL19 | DSM 15313 | Nov. 27, 2002 |
| *Lactobacillus plantarum* HEAL99 | DSM 15316 | Nov. 27, 2002 |

These deposits were made under the provisions of the Budapest Treaty on the International Recognition of the Deposit of Microorganisms for the Purposes of Patent Procedure and the Regulations thereunder (Budapest Treaty). This assures maintenance of a viable culture of the deposit for a period of at least five years after the most recent request for the furnishing of a sample of the deposited microorganism, and in any case for a period of at least thirty (30) years from the date of deposit for the enforceable life of the patent, whichever period is longer. The deposit will be made available by DSMZ under the terms of the Budapest Treaty, and subject to an agreement between Applicant and DSMZ which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited strain is not to be construed as a license to practice the invention in contravention of the rights granted under the authority of any government in accordance with its patent laws.

DETAILED DESCRIPTION OF THE INVENTION

It is totally unexpected according to the present invention that administration of one single strain of *Lactobacillus plantarum* increases the diversity of the gastrointestinal tract, i.e. the total number of different types of bacteria increases in the gastrointestinal tract by giving only one single strain. Thus, it is not only an increased amount of the administered strain that is observed, but also an increase of other bacterial types. Further, the administration and colonization of said single *Lactobacillus plantarum* strain opens up for the growth of new bacterial groups which previously have not been able to grow in the gastrointestinal tract of the individual. This is in contrast to what has been suggested within the art, where it has been suggested that only a mixture of different bacterial strains can provide a mixture of bacterial strains in the gastrointestinal tract, i.e. an increased diversity. Thus, within the technical field it is often objected to giving only one single strain in view of the presumption that the biological diversity is thereby decreased. Put in another way, the main argument for giving mixtures of different types of bacteria is that these mixtures meet the requirement of diversity.

Therefore, it is totally unexpected in accordance with the present invention that administration of only one single strain of *Lactobacillus plantarum* provides an increased diversity.

As stated above, individuals having one or more different physiologically disturbed conditions, as defined below, often simultaneously show LBD (Low Bacterial Diversity), which either is a reason behind the disturbed conditions or is caused by the disturbed conditions. LDB as such is not to be regarded as an ordinary disease condition, but may lead to physiologically disturbed conditions including different diseases or to LIBO (Large Intestine Bacterial Overgrowth) or SIBO (Small Intestine Bacterial Overgrowth) in course of time. Although LIBO and SIBO are not necessarily a result of LBD, this is often the case. An individual having LIBO or SIBO also automatically has LBD in the gastrointestinal tract. LIBO and SIBO are as such also not to be regarded as ordinary disease conditions, but each involves a considerable risk of development of several physiologically disturbed conditions including different diseases, as defined below, e.g. translocation. LIBO and SIBO may alternatively be a result of different physiologically disturbed conditions. The composition according to the present invention may be administered to a healthy individual for prophylactic treatment against developing LBD. Further, said composition may also be administered to an individual having LBD, irrespective of the origin of LBD, for prophylactic treatment against developing one or more physiologically disturbed conditions, SIBO or LIBO. Moreover, said composition may also be administered to an individual having LIBO or SIBO, irrespective of the origin thereof, for prophylactic treatment against developing one or more physiologically disturbed conditions, e.g. translocation. In a further embodiment individuals having LDB and/or SIBO and/or LIBO and at the same time also suffering from one or more of the above-mentioned physiologically disturbed conditions may be subjected to administration with said composition with a view to increasing the bacterial diversity in the gastrointestinal tract and thereby improving the overall health condition of the individual, optionally also alleviating the effects of said one or more physiologically disturbed conditions.

The increased diversity observed in connection with the present invention can be measured in the form of a diversity index measured by the well known T-RFLP method using the enzyme HaeIII for cutting and calculating the Shannon-Weaner and Simpson's indices described below. Said increased diversity index difference is at least 0.15, preferably 0.30, more preferably 0.45, and even more preferably 0.60 when the Shannon-Weaner's index is used.

Said increased diversity index difference is at least 0.02, preferably 0.04, more preferably 0.06 and even more preferably 0.08, when the Simpson's index of diversity is used.

The calculation of the diversity index difference ($Di_{diff\_total}$) is performed by, in a first step, calculating the diversity difference ($Di_{diff}$) of the individuals taking the product containing one strain of Lactobacillus plantarum, i.e. the value of the diversity index after intake ($Di_{after\_product}$) of strain is subtracted by the value of the diversity index before intake ($Di_{before\_product}$), which is divided by ($n_{product}$) being the number of individuals taking the product. Thereafter, the value obtained in the above first step is subtracted by the diversity difference obtained for the placebo ($Di_{placebo\_total} = Di_{after\_placebo} - Di_{before\_placebo}$) divided by $n_{placebo}$ being the number of individuals taking the placebo. The equation for the diversity index difference is as follows:

$$Di_{diff\_total} = \Sigma(Di_{after\_product} - Di_{before\_product})/(n_{product}) - \Sigma(Di_{after\_placebo} - Di_{before\_placebo})/(n_{placebo})$$

The diversity index could, of course, be measured by other known means and a person skilled in the art realizes what such other known means could be. Furthermore, the enzyme used for the cutting, HaeIII, could be replaced by any other known enzyme.

The general health of mankind could become better in view of the increased diversity index provided in the gastrointestinal tract in accordance with the present invention. It has already been discussed above that many physiological disturbances are connected with a low diversity index. By being able to easily take one strain of Lactobacillus plantarum in the form of a solid or liquid formulation, for instance a food product as discussed below, facilitates for individuals to stay healthy.

Furthermore, the increased diversity index provided herein counteracts the negative effects of modern society and welfare state. For instance, as discussed above the huge amount of antibiotics taken worldwide knocks out the balance in the GI tract. This knocked out balance could become normal and healthy again by giving one strain of Lactobacillus plantarum in accordance with the invention.

Furthermore, it is believed that many physiologically disturbed conditions of modern society could be prevented by the continuous intake of one strain of Lactobacillus plantarum in accordance with the invention.

In an embodiment of the invention said composition is a liquid formulation or a solid formulation, wherein said solid formulation is selected from the group consisting of tablets, sucking tablets, sweets, chewing tablets, chewing gums, capsules, sachets, powders, granules, coated particles and coated tablets, enterocoated tablets and capsules, and melting strips and films, and said liquid formulation is selected from the group consisting of oral solutions, suspensions, emulsions and syrups. The composition of the invention may be administered in accordance with any conventional means. However, the strain is preferably administered orally.

In an embodiment of the invention said composition comprises a carrier material, wherein said carrier material is independently selected from the group consisting of oat meal gruel, lactic acid fermented foods, resistant starch, dietary fibres, carbohydrates, proteins, and glycosylated proteins.

In an embodiment of the invention said composition is a medical food, a functional food, a dietary supplement, a nutritional product or a food preparation. Thus, the Lactobacillus plantarum strain may be given to the individuals in many different forms. Said food preparation may be selected from the group consisting of beverages, yoghurts, juices, ice creams, breads, biscuits, cereals, health bars, and spreads. Thus, it is realized that the composition could be easily taken in the form of a food product on a daily basis. Thus, the general health of mankind could become better by the use of the composition according to the invention.

The strain of Lactobacillus plantarum is present in the composition in an amount of about $1 \times 10^6$ to about $1 \times 10^{14}$ CFU (colony forming units), preferably from about $1 \times 10^8$ to about $1 \times 10^{12}$, and more preferably from about $1 \times 10^9$ to about $1 \times 10^{11}$.

The expression "increased diversity difference compared to placebo" used throughout the application text means that the bacterial diversity change of individuals administrated with the Lactobacillus plantarum strains was compared with other individuals who during the time of the study were administrated with a similar product but without the Lactobacillus plantarus strain. These types of studies are blinded, i.e. during the study neither the volunteers nor the persons handling the study and analyzing results know which individual got placebo and which one got treatment product. This rules out many sources of error and false results.

The expression "large intestinal bacterial overgrowth (LIBO)" used throughout the application text means that one or a few bacterial types to a high degree dominates the bacterial flora of the large intestine, i.e. they are present in considerably higher numbers than the majority of other types of bacteria.

The expression "small intestinal bacterial overgrowth (SIBO)" used throughout the application text means that one or a few bacterial types to a high degree dominates the bacterial flora of the small intestine, i.e. they are present in considerably higher numbers than the majority of other types of bacteria.

The expression "low bacterial diversity (LDB)" used throughout the application means an unbalanced bacterial composition in an individual's gastrointestinal tract which may be defined by a diversity index difference of at least 0.15 according to Shannon-Weaner's index of diversity or a diversity index difference of at least 0.02 according to Simpson's index of diversity. It should be noted that the term "diversity" sometimes used in the present application text is intended to mean "bacterial diversity".

The expression "physiologically disturbed conditions" used throughout the application text means any undesired health condition or conditions in connection with or due to the presence of LDB and/or the presence of LIBO or SIBO, such as gastrointestinal disorders, e.g. translocation, Crohn's disease, ulcerative colitis, irritable bowel syndrome and undesired conditions due to antibiotics intake. Furthermore LDB, SIBO and LIBO can be negative factors for development of coronary disorders, non-alcoholic fatty liver disease, diabetes type 2, allergies, atopic eczema and autoimmunity.

The expression "for increasing the diversity of the gastrointestinal tract" used throughout the application text means that an increased flora of micro-organisms in the gastrointestinal tract is obtained in the form of presence of different types of bacteria. This means that the risk of "overgrowth" of certain negative bacteria is decreased, leading to a better general health of individuals. Thus, overgrowth of certain bacteria in the GI tract is decreased in accordance with the invention. Thereby, a desirable balance is provided.

The diversity index is measured by the T-RFLP method using the enzyme HaeIII for cutting and calculating the Shannon-Weaner index and Simpson's index of diversity.

As stated above, the present invention also relates to the treatment of one or a wide array of physiologically disturbed conditions based on a low bacterial diversity (LBD) in the gastrointestinal (GI) tract of an individual, optionally induced via small intestinal bacterial overgrowth (SIBO) and/or large intestine bacterial overgrowth (LIBO), by improving and/or increasing the bacterial diversity and eradicating small intestinal bacterial overgrowth (SIBO) and large intestinal bacterial overgrowth (LIBO) in the gut. LBD is treated by ingestion of one strain of *Lactobacillus plantarum* selected from the group consisting of *Lactobacillus plantarum* 299, DSM 6595, *Lactobacillus plantarum* 299v, DSM 9843, *Lactobacillus plantarum* HEAL-9, DSM 15312, *Lactobacillus plantarum* HEAL-19, DSM 15313, and *Lactobacillus plantarum* HEAL-99, DSM 15316.

*L. plantarum* is a bacterial species in the huge and relatively diverse genus of *Lactobacillus*, which comprises about 90 validly named species or subspecies. By tradition, the *Lactobacillus* spp. have been divided into three functional groups depending on their fermentation abilities; the obligately homofermentatives (Group I), the facultatively heterofermentatives (Group II) and the obligately heterofermentatives (Group III). Group I ferment hexoses exclusively to lactic acid, and cannot ferment gluconate or pentoses, while Group II also ferment hexoses to lactic acid but are additionally able to ferment pentoses and/or gluconate. Group III ferment hexoses to lactic acid, acetic acid and/or ethanol and carbon dioxide. *L. plantarum* is facultatively heterofermentative. The type strain of *L. plantarum* is ATCC 14917.

*L. plantarum* differs from many other *Lactobacillus* spp. in the following points:

1) *L. plantarum* has a relatively large genome, which indicates the ability to adopt to many different conditions.

2) *L. plantarum* possesses a striking ability to ferment many different carbohydrates.

3) *L. plantarum* has a high growth requirement for manganese and can accumulate high intercellular levels of manganese. Manganese provides a defence for *L. plantarum* against oxygen toxicity by the reduction of oxygen radicals to $H_2O_2$. The produced $H_2O_2$ can then be converted to $O_2$ and water by manganese cofactored pseudocatalase.

4) *L. plantarum* has a high tolerance to low pH. The fact that *L. plantarum* frequently predominates in spontaneously, lactic acid fermented foods where the pH usually is below 4.0 and also survives the passage through the acid conditions of the human stomach, points to its high resistance to acid conditions.

5) *L. plantarum* can possess tannase activity and is also able to metabolise phenolic acids.

*L. plantarum* frequently occurs spontaneously, in high numbers, in most lactic acid fermented foods, especially when the food is based on plant material, for example, in brined olives, capers (caper berries), sauerkraut, salted gherkins, sour-dough, Nigerian ogi (made from maize or sorghum), Ethiopian kocho (made from starch from *Ensete ventricosum*), Ethiopian sourdough made out of tef (Eragrostis tef) and cassava. Thus, it is obvious that individuals consuming lactic acid fermented products of plant origin also consume large amounts of *L. plantarum*. Furthermore, *L. plantarum* occurs in grape juice and wine. *L. plantarum* frequently occurs on the human gastrointestinal mucosa, from the mouth to the rectum [Molin, G., Jeppsson, B., Ahrné, S., Johansson, M.-L., Nobaek, S., Ståhl, M., and Bengmark, S. (1993). Numerical taxonomy of *Lactobacillus* spp. associated with healthy and diseased mucosa of the human intestines, *J. Appl. Bacteria* 74: 314-323; Ahrné, S., Nobaek, S., Jeppsson, B., Adlerberth, I., Wold, A., and Molin, G. (1998). The normal *Lactobacillus* flora of healthy human rectal and oral mucosa, *J. Appl. Microbiol.* 85: 88-94)]. Hence, it is obvious that the species *L. plantarum* has a unique position in connection to human food and the human intestine, and in the perspective that humans have eaten lactic acid fermented foods since the beginning as this is a spontaneous process if plant materials are pressed into a closed area, in a pit in the ground, for example, it is understandable that an organisms naturally dominating in these environments also have a key roll to play in the human gut.

EXAMPLES

Measurement of Diversity

Terminal restriction fragment length polymorphism (T-RFLP) analysis is a community fingerprinting method based on the restriction endonuclease digestion of fluorescently end-labelled PCR products, and it reveals information for both known and unknown bacterial groups. T-RFLP patterns are generated in a series of steps: Briefly, community DNA is extracted directly from the sample. The genes of interest are PCR amplified using primers in which one is fluorescently labelled. After purification, the PCR products are digested with a restriction endonuclese, usually a 4-base cutter. The digested product is mixed with a fluorescently labelled DNA size standard, and the fragments are then separated by electrophoresis using either gel or capillary-based systems, equipped with a laser detector so that only the fluorescently labelled terminal fragments are visualized. The output from such an analysis is in two forms: 1) an electropherogram showing the profile of a bacterial community as a series of peaks of varying height, 2) a table generated from an automated fragment analysis program including most importantly the size, in base pairs, and the height (or area) of each peak. The T-RFLP profiles between samples can be numerically compared by using statistical methods. Several statistical methods have been applied to compare microbial communities.

T-RFLP analysis of microbial communities in ecological studies has become increasingly used in recent years. It is reproducible and gives high resolution.

Results

Subjects and Sample Collection

The subjects were all males in good physical condition but with a defined well-controlled cardiovascular disease. They underwent flexible sigmoidoscopy before and after ingestion of test solutions for four weeks. Biopsies were taken in a standardized fashion from mucosa of lower sigmoid colon for further analyses.

16 volunteers were included in the diversity evaluation, derived from a larger cohort of subjects included in a randomized, double blind, placebo controlled study. Nine subjects consumed 100 ml of treatment product per day for four weeks, corresponding to a daily intake of $10^{11}$ colony forming units of L. plantarum per day. Seven subjects consumed 100 ml per day of a similar product but without bacteria for four weeks.

DNA Extraction

The mucosal biopsies were treated in ultrasonic bath for 5 minutes and then vortexed for 2 minutes. The samples were transferred to UV treated 1.5 ml tubes and centrifuged at 9 000 rpm for 7 minutes. 380 µl buffer G2 and 30 µl Proteinas K (Qiagen, Hilden, Germany) were added to the pellet. The samples were treated in water bath at 56° C. until totally dissolved. The suspensions were further disintegrated by shaking together with 12-15 glass beads (2 mm in diameter) for 45 minutes at 4° C. in an Eppendorf Mixer (model 5432, Eppendorf, Hamburg, Germany). After centrifugation at 5 000 rpm for one minute, the supernatant was transferred to two different 2 ml sample tubes (200 µl in each tube). Further purification was done in BioRobot® EZ1 with EZ1 DNA Tissue Card and EZ1 DNA Tissue Kit (Qiagen, Hilden, Germany) according to the manufacturer's instruction. The DNA was eluted in 200 µl.

PCR Amplification, Purification, and Measurement of Concentration

The 16S rRNA gene was amplified with the universal forward primer Cy5-ENV1 (5'-AGA GTT TGA TII TGG CTC AG-3'), fluorescently labeled with Cy5 at the 5' end, and the reverse primer ENV2 (5'-CGG ITA CCT TGT TAC GAC TT-3'), which anneal with 8-27 bp and 1511-1492 bp, respectively. The PCR reaction mixture contained 0.2 µM of each primer, 0.2 mM of each deoxyribonucleotide triphosphate (Roche Diagnostics, Indianapolis, Ind.), 5 µl of 10×PCR reaction buffer (100 mM Tris-HCl, 500 mM KCl, pH 8.3), 2.5 U/µl Taq polymerase (Roche Diagnostics, Mannheim, Germany) and 0.2-10 µl of template, in a final volume of 50 µl. Amplification was made in an Eppendorf Mastercycler (Hamburg, Germany) using the following program: one cycle at 94° C. for 3 minutes, followed by 32 cycles at 94° C. for 1 min, 50° C. for 45 sec and 72° C. for 2 min, with an additional extension at 72° C. for 7 min.

PCR products (5 µl) were verified on a 1.5% (w/v) agarose gel in 1×TBE buffer (89 mM Tris, 89 mM boric acid, 2.5 mM EDTA) after staining with ethidium bromide.

PCR products from three reactions were pooled to reduce bias in PCR and to get enough DNA for T-RFLP analysis. The amplicons were purified and concentrated by MinElute PCR Purification Kit (Qiagen, Hilden, Germany) according to the manufacturer's protocol. Elution was made with 30 µl of sterile distilled water.

The concentration of the purified DNA was measured spectrofluorometrically by FluoroMax-2 with DataMax for Windows™ (ISA Jobin Yvon Spex Instruments S.A., Inc., New Jersey), using Quant-iT™PicoGreen®(Invitrogen, Eugen, Oreg., USA) that intercalates with double stranded DNA. The QuantiT™PicoGreen® was used according to the manufacturer's instruction. Excitation was performed at 480 nm.

T-RFLP Analysis

Aliquots of 200 ng purified PCR products were digested during 16 hrs at 37° C. separately with 15 U of restrictionendonuclease HaeIII (Sigma-Aldrich, St Louis, USA), in a total volume of 10 µl. After digestion, the enzymes were inactivated by heating at 65° C. for 15 min. The digests were mixed with 1 µl of internal size standard and 4 µl of formamide loading dye (3.3 µl deionised formamide, 0.7 µl 25 mM EDTA with 5% w/v Dextran Blue) and the mixture was denatured at 94° C. for 3 min and then immediately placed on ice, prior loading to the polyacrylamide gel.

The internal size standards contained Cy5-ENV1 primer (20 bp as described above) and 697 bp PCR product amplified from E. coli ATCC 11775 by using primer 685r (5'-TCT ACG CAT TTC ACC GCT AC-3'; E. coli numbering 705-685) and Cy5-ENV1. External size standards, consisting of ALFexpress Sizer 50-500 (GE Healthcare, Uppsala, Sweden) and Cy5 labeled 697 bp PCR product, were also loaded on the sample-containing polyacrylamide gels to estimate the lengths of the T-RFs. The fluorescently labelled fragments were separated and detected with an ALFexpress II DNA sequencer with a 7% ReproGel Long Read gel (GE Healthcare, Uppsala, Sweden) for 700 min under the following conditions: 1500 V, 60 mA, and 55° C.

Statistical Analysis

The peak areas of fluorescently labelled T-RFs were estimated by using ALFwin™ Fragment Analyser 1.03 program (Amersham Biosciences, Uppsala, Sweden). The relative abundance of each T-RF within a given T-RFLP pattern was calculated as the peak area of the respective T-RF divided by the total peak area of all T-RFs detected within a fragment length between 20 to 697 bp. Simpson's (D) and Shannon-Weaner (H') indices were calculated by using the equations: $D=\Sigma p_i^2$ and $H'=-p_i \ln p_i$, where $p_i$ is the relative abundance of ith peak in the community (Magurran A, 1996), Ecological diversity and its measurement, Chapman and Hall, London. The use of Simpson's index of diversity (1-D) instead of the original formulation of Simpson's index ensures that the value of the index increases with increased diversity. For each individual, indices were calculated for the samples before and after treatment. The difference in diversity was obtained by subtracting index before treatment from index after treatment. The differences in the bacterial diversity between individuals in the probiotic and placebo groups were detected using Mann-Whitney Rank Sum Test (SigmaStat, Systat Software, Point Richmond, USA). A p value of <0.05 was considered statistically significant.

When analysing the data from the T-RFLP profiles a statistically significant difference in diversity of the intestinal microbiota in individuals treated with L. plantarum 299v during four weeks was found compared to individuals who received placebo. The restriction endonuclease HaeIII was used as the cutting enzyme and the mean difference in diversity as measured by Shannon index was 0.2305803 for the probiotic group and -0.3929243 for the placebo group (p=0.026).

Calculating Simpson's Index of diversity confirmed the higher diversity by giving L. plantarum 299v. HaeIII was used as the cutting enzyme and the result was statistically significant, the mean difference by Simpson's Index of Diversity was 0.0367907 for the probiotic group and -0.04792 for the placebo group (p=0.026).

Mean Difference in Diversity Indices

|  | Shannon | Simpson's |
| --- | --- | --- |
| $Di_{before\ 299v} - Di_{after\ 299v}$ | 0.2305803 | 0.0367907 |
| $Di_{before\ placebo} - Di_{after\ placebo}$ | -0.3929243 | -0.04792 |
| $Di_{total}$ | 0.6235046 | 0.0847107 |
| Significance of $Di_{total}$ | P = 0.026 | P = 0.026 |

The results above show that the bacterial diversity of the human gut increases when administrated a single strain of Lactobacillus plantarum, i.e. between individuals given the Lactobacillus plantarum strain and individuals given a placebo.

The invention claimed is:

1. A method of increasing bacterial diversity in the gastrointestinal tract of a human individual the method comprising orally administering to the individual a composition comprising about $1 \times 10^6$ to about $1 \times 10^{14}$ colony forming units (CFU) of a strain of Lactobacillus plantarum selected from the group consisting of Lactobacillus plantarum 299 deposited under accession number DSM 6595; Lactobacillus plantarum 299v deposited under accession number DSM 9843; Lactobacillus plantarum HEAL 9 deposited under accession number DSM 15312; Lactobacillus plantarum HEAL 19 deposited under accession number DSM 15313; and Lactobacillus plantarum HEAL 99 deposited under accession number DSM 15316, wherein said administration of said strain of Lactobacillus plantarum produces an increased bacterial diversity index difference in the gastrointestinal tract of said individual compared to placebo, wherein said increased bacterial diversity index difference is measured by the T-RFLP (Terminal Restriction Fragment Length Polymorphism) method using HaeIII restriction as enzyme and the Shannon-Weaner and Simpson's indices.

2. The method according to claim 1, wherein said increased diversity index difference is at least 0.15 when the Shannon-Weaner's index is used.

3. The method according to claim 2, wherein said increased diversity index difference is at least 0.30.

4. The method according to claim 2, wherein said increased diversity index difference is at least 0.45.

5. The method according to claim 2, wherein said increased diversity index difference is at least 0.60.

6. The method according to claim 1, wherein said increased diversity index difference is at least 0.02 when the Simpsons's index is used.

7. The method according to claim 6, wherein said increased diversity index difference is at least 0.04.

8. The method according to claim 6, wherein said increased diversity index difference is at least 0.06.

9. The method according to claim 6, wherein said increased diversity index difference is at least 0.08.

10. The method according to claim 1, wherein said composition is a liquid formulation or a solid formulation.

11. The method according to claim 10, wherein said solid formulation is selected from the group consisting of a tablet, a sucking tablet, a sweet, a chewing tablet, a chewing gum, a capsule, a sachet, a powder, a granule, a coated particle, a coated tablet, an enterocoated tablet, an enterocoated capsule, a melting strip and a film.

12. The method according to claim 10, wherein said liquid formulation is selected from the group consisting of an oral solution, a suspension, an emulsion and a syrup.

13. The method according to claim 1, wherein said composition is a medical food, a functional food, a dietary supplement, a nutritional product or a food preparation.

14. The method according to claim 13, wherein said food preparation is selected from the group consisting of a beverage, a yoghurt, a juice, an ice cream, a bread, a biscuit, a cereal, a health bar, and a spread.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)..(1)
<223> OTHER INFORMATION: fluorescently labeled with Cy5 at the 5' end
<220> FEATURE:
<221> NAME/KEY: modified_base
<222> LOCATION: (11)..(11)
<223> OTHER INFORMATION: n=I
<220> FEATURE:
<221> NAME/KEY: modified_base
<222> LOCATION: (12)..(12)
<223> OTHER INFORMATION: n=I

<400> SEQUENCE: 1
agagtttgat nntggctcag                                             20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: modified_base
<222> LOCATION: (4)..(4)
<223> OTHER INFORMATION: n=I

<400> SEQUENCE: 2
cggntacctt gttacgactt                                             20

<210> SEQ ID NO 3
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 3
tctacgcatt tcaccgctac                                             20
```